Figure 1:
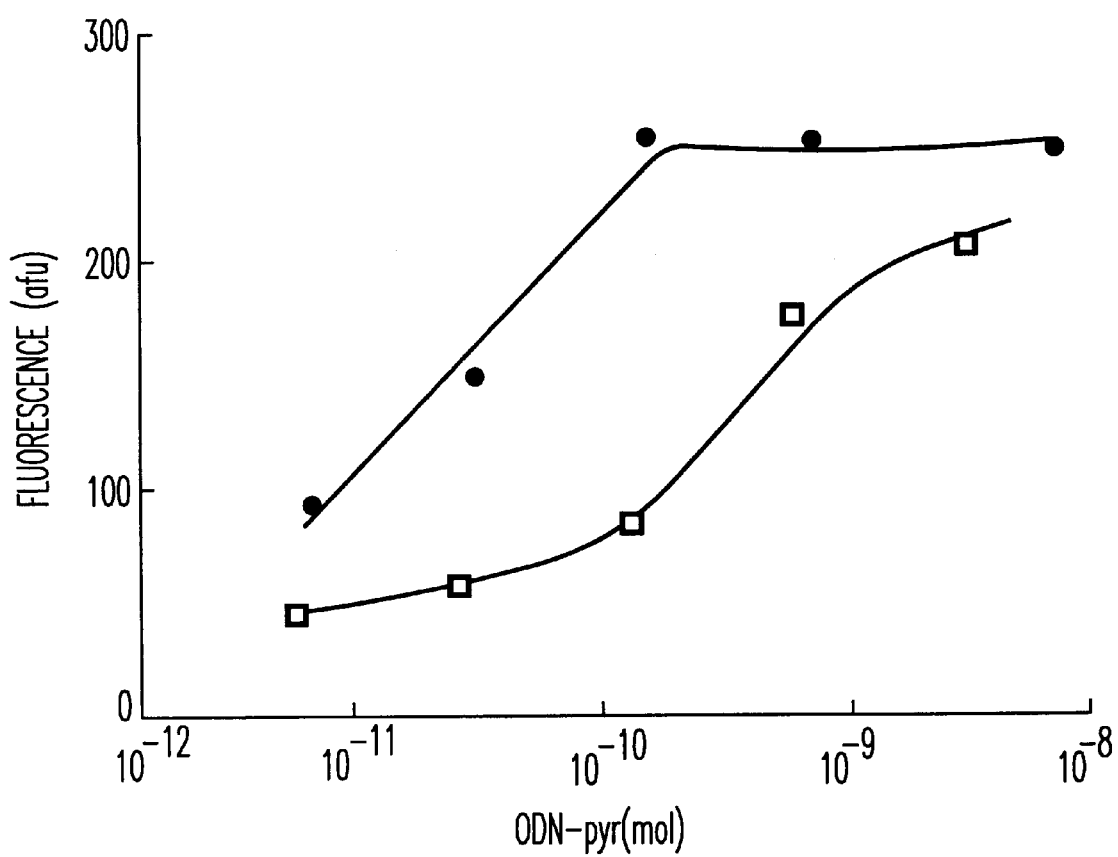

United States Patent [19]

Marchand et al.

[11] Patent Number: 6,160,103
[45] Date of Patent: Dec. 12, 2000

[54] CONJUGATES OF AN OLIGONUCLEOTIDE/ELECTRONIC CONDUCTOR POLYMER WITH A MOLECULE OF INTEREST, AND THEIR USES

[75] Inventors: Joseph Marchand, Orsay; Hervé Bazin, Impasse Laennec, both of France

[73] Assignee: Cis Bio International, Saclay, France

[21] Appl. No.: 09/147,420

[22] PCT Filed: Jun. 25, 1997

[86] PCT No.: PCT/FR97/01134

§ 371 Date: Dec. 21, 1998

§ 102(e) Date: Dec. 21, 1998

[87] PCT Pub. No.: WO97/49718

PCT Pub. Date: Dec. 31, 1997

[30] Foreign Application Priority Data

Jun. 25, 1996 [FR] France .................................. 96 07846

[51] Int. Cl.[7] .......................... C07H 21/02; C07H 19/00; C07K 1/00; C07K 14/00; C07K 16/00

[52] U.S. Cl. ..................... 536/23.1; 536/22.1; 536/24.1; 530/402; 435/5; 435/6

[58] Field of Search .......................... 435/5, 6; 536/22.1, 536/23.1, 24.1, 25.3; 530/402

[56] References Cited

FOREIGN PATENT DOCUMENTS

WO94/22889  10/1994  WIPO .
WO95/29199  11/1995  WIPO .

OTHER PUBLICATIONS

Solomons "Organic Chemistry, Fifth Edition" John Wiley and sons, Inc. pp. 997–1000, 1992

*Primary Examiner*—Jezia Riley
*Attorney, Agent, or Firm*—Oblon, Spivak, McClelland, Maier & Neustadt, P.C.

[57] ABSTRACT

The invention concerns a macromolecule of formula (I): P-O-M in which M represents a molecule of interest, O represents an oligonucleotide chain; P represents a monomer of an electronic conductor polymer, and x and y are integers equal to 1 or more. The invention also concerns the copolymers obtained from the P-O-M macromolecules.

17 Claims, 2 Drawing Sheets

CONJUGATES OF AN OLIGONUCLEOTIDE/ELECTRONIC CONDUCTOR POLYMER WITH A MOLECULE OF INTEREST, AND THEIR USES

The present invention relates to novel methods and novel compounds for controlling the attachment of different molecules of interest to an electronically conductive polymer (ECP);

The application PCT WO 94/22889 in the name of CIS BIO INTERNATIONAL (inventors, TEOULE et al.) describes the attachment of oligonucleotides to a support which consists of an electronically conductive polymer (ECP).

This attachment can be effected in a variety of ways:

1) by the attachment of a presynthesized oligonucleotide to the ECP (that is by chemically reacting the oligonucleotide on the previously functionalized ECP or by copolymerizing ECP monomers with the product of the condensation of the oligonucleotide on one of the said monomers).

2) by elongation of the oligonucleotide starting with one nucleoside, one nucleotide or one oligonucleotide which has already been attached to the ECP using, for example, one of the standard methods for synthesizing nucleic acids.

The attachment of oligonucleotides to ECPs facilitates the isolation and use of oligonucleotide matrices which can, in particular, be employed for sequencing nucleic acids and for diagnosis.

Just like oligonucleotide matrices, peptide matrices and, more generally, matrices of various molecules represent a particularly advantageous tool, for example in the field of diagnosis or for screening active molecules. It would therefore be desirable for other types of matrix to be able to benefit from the improvements brought about by using ECPs.

However, the attachment of molecules of interest other than oligonucleotides, for example the attachment of peptides, to an ECP poses more problems than does the attachment of oligonucleotides.

Thus, although methods for synthesizing pyrrole carrying an amino acid or a dipeptide are described in the literature [GARNIER et al. J. Am. Chem. Soc., 116, 8813–8814 (1994)], these are methods for carrying out synthesis in solution, which methods do not in practice enable synthetic peptide molecules of a size greater than 2 or 3 amino acids to be obtained in sufficient yield. However, molecules which are of real interest within the field of diagnosis or that of screening active molecules are longer; for example, a "minimal" antigenic motif generally contains an average of 6 amino acids.

The usual methods of synthesizing peptides on a solid support, which methods are derived from the MERRIFIELD technique, involve the use of different groups for protecting the side chains of the amino acids. The elimination of these groups, and the separation of the peptide and support at the conclusion of the synthesis are effected in strong acid medium (hydrofluoric acid or trifluoroacetic acid). However, ECP monomers, in particular the pyrrole residue, have a tendency to polymerize in acid medium, thereby creating undesirable by-products.

It seems, therefore, that neither the synthesis method which is carried out in solution, and whose possibilities are limited to synthesizing dipeptides or tripeptides, nor synthesis on a support, whose implementation requires chemical conditions which are incompatible with the stability of the pyrrole residue, are suitable for synthesizing peptides which are modified by a pyrrole residue.

It is nevertheless possible to graft an ECP monomer, for example a pyrrole residue, onto a preformed oligopeptide which has been obtained by traditional peptide synthesis on a solid phase. This grafting can be effected using known methods, for example by reaction between a carboxylic derivative of the pyrrole (activated by a coupling reagent) and one of the available amino functions of a peptide (for example the amino function at the N-terminal end), in accordance with the following scheme [S. E. WOLOWACZ et al., Anal. Chem., 64, 1541–1545, (1992)]. Pyrrole—COOR+NH2—peptide→Pyrrole—CONH—peptide At the conclusion of the reaction, the pyrrole-peptide conjugate has to be isolated from the reaction mixture containing the unreacted peptide and pyrrole as well as any possible salts and by-products.

The various methods which it might therefore be possible, a priori, to envisage using for this purpose are those which are customarily employed for purifying peptides, in particular reverse-phase chromatography methods (RP-HPLC), or gel filtration.

The simplest way to detect the peptides at the conclusion of the chromatography is to measure the ultraviolet absorption at a wavelength of from 215 nm to 220 nm; this is because all peptides absorb light at this wavelength. However, this approach of measuring absorption in the region of 215 nm suffers from the drawback of being relatively insensitive and of not being specific since solvents and organic or inorganic ions are also detected.

Methods exist which enable the peptides to be detected specifically by an "in-line" chemical reaction at the outlet of the chromatography column. While this method has the advantage of increasing the sensitivity of the detection, it makes this detection more cumbersome and, furthermore, irreversibly modifies the peptide; this modification can, in particular, have significant consequences for its functional properties (for example its antigenicity).

The problems expounded above with regard to peptides also arise when detecting other molecules of interest, etc. Thus, a large number of substances, such as sugars, polysaccharides or steroids, either do not exhibit any specific absorption at a defined wavelength in the UV or only exhibit weak absorption which in turn prejudices the sensitivity of the detection.

One is therefore obliged to use an appropriate physical or chemical means to detect the presence of the sought-after molecule in each fraction derived from the chromatography, something which, quite obviously, takes a large amount of time; furthermore, this analysis often destroys the analyte in question.

The object of the present invention is that of obtaining conjugates, which are easy to synthesize and purify, and molecules of interest with an ECP monomer. With this aim, the inventors have prepared conjugates which possess properties which are not naturally possessed either by the molecule of interest or by the ECP monomer.

In these conjugates, the molecule of interest and the ECP monomer are linked by way of an oligonucleotide chain which serves as a spacer arm between the ECP monomer and the molecule of interest under consideration.

The present invention relates to a macromolecule of the following formula (I):

$$P-O-M \qquad (I)$$

in which:

M represents a molecule of interest;

O represents an oligonucleotide chain;

P represents a monomer of an electronically conductive polymer.

Within the meaning of the present invention, a "molecule of interest" is understood as being any molecule which exhibits a useful functionality in reactions carried out on a solid support, for example synthesis reactions or direct or indirect detection reactions. This molecule of interest can, for example, without this list being limiting, be a biomolecule, such as a protein (in particular an enzyme), an amino acid, a peptide, a glycopeptide, a lipid, a steroid, a glycolipid, a sugar, a polysaccharide, a molecule which is able, directly or indirectly, to generate a signal, or else a complex, multifunctional molecule, etc. Advantageously, this molecule of interest is one of the members of an affinity couple and can, for example, be biotin or a potentially antigenic peptide, etc.

P can, for example, be a monomer of polyacetylene, of polyazine, of poly(p-phenylene), of poly(p-phenylene vinylene), of polypyrene, of polypyrrole, of polythiophene, of polyfuran, of polyselenophene, of polypyridazine, of polycarbazole, of polyaniline, etc.

Advantageously, P is a pyrrole group.

The oligonucleotide chain O can consist of an assembly of natural nucleotides and/or nucleotide analogues, such as those described, for example, by UHLMANN, [Chemical Review, 90:4, 543–584 (1990)]. It can be a single-stranded oligonucleotide or a double-stranded oligonucleotide over at least a part of its length. In the second case, one of the strands is covalently attached to the P monomer and the other strand is covalently attached to the molecule of interest M.

In theory, there is no limit to the nature or length of the oligonucleotide; in practice, the oligonucleotide chain advantageously has a length of between 6 and 60, preferably between 10 and 30, nucleotides. Advantageously, the percentage of (G+C) in the oligonucleotide O is less than or equal to 70%, preferably less than or equal to 50%.

The attachment of the oligonucleotide O to the ECP monomer can be effected as described in application PCT WO 94/22889. The attachment of the molecule of interest M to the oligonucleotide O can be effected by means of various methods, which are known per se, for linking an oligonucleotide to another molecule. The choice of the most appropriate method essentially depends on the nature of the molecule of interest M.

For example, the oligonucleotide O can be activated by attaching an ester of N-hydroxysuccinimide, an amino acid, an SH group [ARAR et al., Bioconjugate Chem. 6, p. 573–577, (1995)] or a maleimide group.

The present invention also relates to a process for preparing a macromolecule P-O-M as defined above from a mixture which comprises the said macromolecule and also the P-O and M reagents from which it was formed, which process is characterized in that it comprises at least one step during which the said mixture is fractionated by any means which make it possible to separate the fractions comprising M and P-O-M, respectively, from the fraction comprising P-O, and a step during which the fraction comprising P-O-M is detected and/or the quantity of P-O-M is determined by detecting and/or measuring a parameter which is associated with the oligonucleotide O and not associated with the molecule of interest M.

By its chemical nature and its length, the oligonucleotide chain O plays a role in the physical properties (polarity in chromatography, for example) of the conjugate with the molecule of interest under consideration, a fact which makes it possible to arrange optimum separation of the resulting conjugate from the excess reagents. Moreover, the oligonucleotide chain enables the conjugate to be detected specifically at a wavelength of between 240 and 270 nm (advantageously 265 nm) in the ultraviolet and, where appropriate, by means of hybridization with an oligonucleotide having a complementary sequence.

The properties conferred by the oligonucleotide chain O thus permit easy manipulation of minute quantities of molecules of interest by facilitating their separation using ultrafiltration and/or partition chromatography methods or methods of affinity chromatography on oligonucleotides having a complementary sequence, and their detection and rapid quantification by means of measuring specific absorption between 240 and 270 nm. This is particularly advantageous when the molecule of interest M is a peptide; this is because measuring the absorption of the oligonucleotides at 265 nm is much more sensitive and specific (there is no interference from salts and solvents) than measuring the absorption of the peptides at 205 nm.

The present invention also relates to copolymers at least one of the units of which consists of a macromolecule P-O-M as defined above.

Polymers in accordance with the invention are, for example, defined by one of the following formulae (II), (III) or (IV):

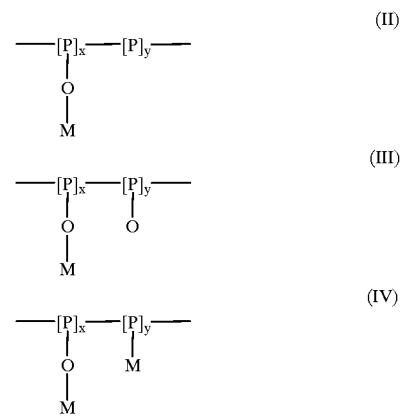

in which:

x and y represent integers equal to or greater than 1, and

M represents a molecule of interest;

O represents an oligonucleotide chain

P represents a monomer of an electronically conductive polymer.

In a copolymer according to the invention, the electronically conductive polymer monomers P may be identical to each other or else differ from each other; the oligonucleotides O may also be identical to each other or differ in their sequence and/or their size and/or their single-stranded or double-stranded nature; similarly, the M molecules may be identical or different from each other.

These copolymers may be prepared by copolymerizing one or more purified P-O-M conjugate(s), or such as defined above, with P monomers and/or with P-O conjugates, such as those described in application PCT WO 94/22889, and/or with P-M conjugates; they may also be obtained by attaching one or more molecules of interest M to all or some of the oligonucleotide side chains of an ECP/oligonucleotide copolymer such as those described in application PCT WO 94/22889. This attachment may, for example, be effected by covalently linking a molecule of interest M to an oligonucleotide O which is itself attached to the ECP, or else by way of an oligonucleotide which is hybridized to the said oligonucleotide O along at least some of its length.

The copolymers according to the invention may be used in all the applications in which it is customary to attach molecules of interest to a solid support, in particular to an electrode.

The present invention relates to electrodes whose surface carries at least one copolymer in accordance with the invention.

For example, the surface of an electrode in accordance with the invention may be entirely covered with one single copolymer in accordance with the invention; it may also carry several copolymers which are in accordance with the invention and which differ from each other by at least one of the constituents P, O or M; this or these copolymers may also be associated, on the same electrode, with other polymers, for example ECP/oligonucleotide copolymers such as those described in application PCT WO 94/22889 or else with polymers of a different nature, such as, for example, ECPs which result from polymerizing P monomers such as defined above.

Polymers in accordance with the invention can be used for building matrices of molecules of interest, in particular electrode matrices which comprise at least one electrode in accordance with the invention, such as defined above.

Electrodes which constitute different points of one and the same matrix may differ from each other in the P monomers which are included in the composition of the copolymers which are present on their surface and/or in the O oligonucleotide and/or the M molecules of the side chains of these copolymers; they may also differ from each other in the quantity of these side chains per unit of surface area.

Some of the electrodes of one and the same matrix may carry a polymer other than a copolymer in accordance with the invention, for example an ECP/oligonucleotide copolymer such as those described in application PCT WO 94/22889. Depending on the envisaged use, this ECP/oligonucleotide copolymer may be retained as such or else used for attaching other molecules of interest, either directly or by means of hybridization with another oligonucleotide which carries the molecule of interest.

Such matrices may be prepared by depositing desired polymers in a targeted manner on pre-defined electrodes; for example, copolymers in accordance with the invention may be deposited by the targeted electrochemical copolymerization, on selected electrodes, of P-O-M conjugates and/or of variable quantities of one and the same P-O-M conjugate with P monomers and, where appropriate, P-O and P-M conjugates. The use of macromolecules P-O-M and copolymers in accordance with the invention therefore makes it possible to obtain multifunctional matrices in a simple manner.

The P-O-M conjugates in accordance with the invention may also be used for calibrating oligonucleotide matrices which are attached to an electronically conductive polymer support. Thus, the inventors observed that it was possible to establish a reproducible correlation between the quantity of O-M side chains and the quantity of oligonucleotides attached to an electronically conductive polymer support. Consequently, measuring the attachment of O-M side chains to an electrode under given experimental conditions makes it possible to anticipate the quantity of oligonucleotides which will be attached to another electrode (of the same matrix or of another matrix) under the same experimental conditions.

The use of P-O-M conjugates and copolymers in accordance with the invention makes it possible to obtain electrodes which constitute internal controls, making it possible qualitatively and/or quantitatively to monitor the attachment of molecules X to a solid support which consists of the surface of an electrode which carries an electronically conductive polymer. This monitoring of the attachment of molecules X can be effected at any time (after these molecules have been deposited or while these molecules are being used). The molecules X whose attachment can be detected by using a copolymer in accordance with the invention may be of a variety of natures; advantageously, they comprise at least one oligonucleotide chain O and/or one molecule of interest M which can be identical to, or different from, those of the copolymer in accordance with the invention which is employed.

A polymer in accordance with the invention can be employed for detecting and/or quantifying a molecule X which constitutes one of the side chains of the same polymer, or else of a polymer of the same formula, which has been deposited on the same electrode or else on another electrode of the same matrix or of a different matrix. It can also be employed for detecting and/or quantifying a molecule X which belongs to a different polymer, which may also be deposited on the same electrode or on another electrode of the same matrix or of a different matrix.

This detection and/or quantification can be effected, for example, by detecting oligonucleotide chains O of the copolymers in accordance with the invention by means of hybridization with a labelled probe or else by using, on one or more of the electrodes of the matrix, copolymers in accordance with the invention which comprise a molecule of interest M which constitutes a readily detectable label (for example biotin or a fluorescent label).

The present invention will be better understood with the aid of the remainder of the description which follows and which refers to examples of preparing and using macromolecules and copolymers in accordance with the invention.

EXAMPLE 1

Spectral and Chromatographic Properties of Peptides

A commercially available synthetic peptide (Cat. No. A2532 SIGMA-ALDRICH Chimie), which has a molecular mass of 1652.1 daltons and which corresponds to ACTH (adrenocorticotrophic hormone) fragment 11-24, is used to illustrate the problems posed by detecting a peptide of biological interest. According to the manufacturer's specifications, the peptide content of the preparation is 61%.

25 $\mu$l of a 2 mg/ml solution of the said peptide are injected onto LICHROSPHER® RP-18E 5 $\mu$m 125-4 a HPLC column (MERCK, DARMSTADT, Germany). The column is eluted (1 ml/min) in 35 minutes with the mixture A+B, (A=5% ACN (acetonitrile), 25 mM TEAAc (triethylammonium acetate); B=50% ACN, 25 mM TEAAc) using a gradient of from 0% to 100% B.

A peak at a retention time Rt=2 minutes and a relatively broad peak at Rt=10 minutes are observed. The fractions corresponding to these two peaks are collected, concentrated and analysed.

Fraction F1 (Rt=2 minutes) exhibits an absorption at $A_{220\ nm}$=1.033. On the other hand, $A_{275\ nm}$ is of the same order as the background noise (0.005). This fraction therefore contains salts (non-specific $A_{220\ nm}$).

Fraction F2 (Rt=10 minutes) exhibits an absorption at $A_{220\ nm}$=1.90 and at $A_{275\ nm}$=0.073. This fraction therefore contains the peptide.

This illustrates the fact that UV detection in the region of 215 to 220 nm does not, by itself, enable the signal on the chromatogram due to the peptide to be differentiated from the interfering signals of other substances.

The commercial synthetic peptide (Cat. No. A 0673, SIGMA-ALDRICH CHIMIE), which has a molecular mass of 2465.7 daltons and which corresponds to ACTH fragment (18-39), was analysed in the same way by means of RP-HPLC. According to the manufacturer, the peptide content of the sample is 82%.

The HPLC analysis is carried out under the same conditions as above and the fractions are detected in the UV at 215 nm.

One major peak having an Rt=18.45 minutes is observed; this peak is narrower than that observed with ACTH fragment (11-24).

This experiment demonstrates that two different peptide fragments exhibit peaks which are characterized by very different retention times. Comparison of the HPLC profiles also shows that the peaks may be broadened, as in the case of ACTH (11-24).

EXAMPLE 2
Synthesis of an Oligonucleotide Which is Modified Both with a Pyrrole Residue and with an Aminoalkyl Arm A modified oligonucleotide having the sequence:

5'HO-dC$^{pyrrole}$-(T)$_{10}$-p-dC$^{aminohexyl}$-p-dTOH3' is synthesized on a solid support (CPG (controlled-pore glass)) using the "phosphite-phosphoramidite" method described by BEAUCAGE and LYER [Tetrahedron., 48, 2223–2311, (1992)].

The main steps of this synthesis are described below.

An aminoalkyl-phosphoramidite derived from 5'-O-(4,4'-dimethoxytrityl)-N-4-(6-aminohexyl)-2'-deoxycytidine [ROGET et al. Nucleic Acids Res., 17, 7643–7650, (1989)] is prepared.

This aminoalkyl-phosphoramidite is obtained in two steps: the primary amine of the alkylamine arm carried by the nucleoside is protected with a trifluoroacetyl group, after which the 3' hydroxyl is phosphitylated using a method which is analogous to that described by SPROAT et al. [Nucleic Acids Res. 15, 6181–6196, (1987)], in the case of the phosphoramidite of 5'-trifluoroacetamido-2',5'-dideoxythymidine [lacuna] by SPROAT et al. [Nucleic Acids Res. 15, 6181–6196, (1987)].

The aminoalkyl-phosphoramidites which are thus obtained are coupled on a column of a DNA synthesizer by way of thymidines which have been previously attached to this column.

Other aminoalkyl-phosphoramidites, such as those described by AGRAWAL et al. [Nucleic Acids Res., 14, 6227, (1986)]; CONNOLLY, [Nucleic Acids Res. 15, 3131, (1987)]; and BEAUCAGE and LYER [Tetrahedron. 49, 1925–1963, (1993)] can also be used.

The phosphoramidite of the thymidine is then condensed with the aminoalkyl-phosphoramidite which is attached to the column. This step is repeated until a 10-mer oligonucleotide chain has been obtained.

A phosphoramidite of 5'-O-(4,4'-dimethoxytrityl)-N-4-(6-aminohexyl)-2'-deoxycytidine, to which a pyrrole residue has been grafted in accordance with the protocol described in application PCT WO 94/22889 and by LIVACHE et al., [Nucleic Acids Res. 22, 2915–2921, (1994)], is condensed onto the 5' end of the resulting oligonucleotide.

The oligonucleotide is deprotected in concentrated ammonia (55° C. for 16 hours) and purified by HPLC on a LICHROSPHER® RP-18E 250-10 (10 µm) column (MERCK, DARMSTADT, Germany) using a gradient of acetonitrile in 50 mM triethylammonium acetate (buffer A; 5% acetonitrile, buffer B: 50% acetonitrile; flow rate 5 ml/minute, gradient of 10% B to 25% B in 20 minutes), in accordance with the method described in: "Oligonucleotide synthesis: A practical approach, Ed M. J. Gait. IRL Press, Oxford".

The fractions corresponding to a major peak (retention time greater than 15 minutes) are evaporated. After evaporation, the oligonucleotide which has been obtained is desalinated by filtering it through an NAP-5® column (PHARMACIA-LKB BIOTECHNOLOGY, UPPSALA, Sweden).

EXAMPLE 3
Preparation of an Active Oligonucleotide in the Form of an N-Hydroxysuccinimide Ester The modified oligonucleotide (designated pyr-T$_{10}$-NH2 below), prepared in accordance with the method described in Example 2 above, is converted into its corresponding activated intermediate (N-hydroxysuccinimide ester) in accordance with the following protocol:

The lyophilized oligonucleotide pyr-T$_{10}$-NH2 (10 to 25 nmol) is taken up in 12 µl of 50 mM N-(3-sulphopropyl) morpholine (MOPS) buffer, pH 7.0. 28 µl of dimethylformamide containing 4 µmol of disuccinimidyl suberate (DSS, PIERCE ROCKFORD, Ill.) are added to this solution and the mixture is then left to stir mechanically (16 hours at 4° C. or 5 hours at 20° C.). The reaction mixture is loaded onto an NAP-5® column which has been equilibrated with water and the column is eluted with water in accordance with the protocol recommended by the manufacturer. The excluded fraction (1 ml) is extracted 5 times with 1 ml of n-butanol. At each extraction, the mixture is centrifuged, after which the upper (organic) phase is discarded and the lower (aqueous) phase is retained. After the last extraction, the N-hydroxysuccinimide ester (designated pyr-T$_{10}$-NHS below), which has sedimented to the bottom of the tube, is dried in vacuo (SPEED-VAC) and then stored at −20° C. (preferably for less than 24 hours) until it is used.

An analytical HPLC on a LICHROSPHER® RP-18E/125-4 (5 µm) column (MERCK, DARMSTADT, Germany) is carried out on an aliquot of the reaction mixture at different reaction times; a gradient of acetonitrile in 50 mM triethylammonium acetate (buffer A: 5% acetonitrile, buffer B: 50% acetonitrile) is used for the elution; flow rate, 1 ml/min, gradient of 10% B to 30% B in 20 minutes, then of 30% B to 50% B in 15 minutes. This chromatographic analysis shows the disappearance of the pyr-T$_{10}$-NH$_2$ oligonucleotide peak (retention time, approximately 19 minutes) and the appearance of a peak (retention time, approximately 27 minutes) corresponding to the N-hydroxysuccinimide ester (designated pyr-T$_{10}$-NHS).

EXAMPLE 4
Coupling a Modified Oligonucleotide to Peptides
A) Coupling to the ACTH(11-24) Fragment 20 nmol of pyr-T$_{10}$-NHS, obtained as described in Example 3, are taken up in 50 ml of MOPS buffer (50 mM, pH 7.8). The ACTH(11-24) peptide (SIGMA, St Louis, United States) (26 nmol, 1.3 eq.) is added in 50 µl of MOPS buffer, pH 7.8. The mixture is incubated at 4° C. overnight.

The disappearance of pyr-T$_{10}$-NHS and the appearance of a major peak corresponding to the oligonucleotide-peptide conjugate (retention time, approximately 26.4 minutes) are seen in an analytical HPLC which is carried out under conditions which are identical to those of Example 3.

The reaction mixture is purified by semi-preparative HPLC carried out on a LICROSPHER® RP-18E/125-4 (5 µm) column using a gradient of acetonitrile in 50 mM triethylammonium acetate. The elution is carried out under the same conditions as the analytical HPLC described in Example 3.

The oligonucleotide-peptide conjugate is detected, by measuring the UV absorbance at 265 nm, and collected in the fraction corresponding to a retention time of between 24 and 25.5 minutes; this fraction is dried by evaporation (SPEED-VAC). This results in approximately 3.7 nmol of conjugate designated pyr-$T_{10}$-ACTH(11-24).

B) Coupling to the ACTH(18-39) Fragment

The oligonucleotide ester pyr-$T_{10}$-NHS (EX.3) (approximately 20 nmol) is coupled to approximately 35 nmol, that is approximately 1.8 eq., of the ACTH(18-39) fragment (SIGMA, St Louis, United States), and the coupling product, designated pyr-$T_{10}$-ACTH(18-39) is purified using the protocols described in A) above.

The pyr-$T_{10}$-ACTH(18-39) conjugate is detected in the fraction corresponding to a retention time of between 26 and 27 minutes. After this fraction has been dried, approximately 7 nmol of the conjugate are obtained.

EXAMPLE 5
Synthesis of a Pyrrole-$T_{10}$-Biotin Conjugate

A modified oligonucleotide having the sequence pyr-$T_{10}$-NH2 (from 10 to 20 μmol) is treated with an excess of biotin-NHS (approximately 50 equivalents) (SIGMA) dissolved in 20 μl of dimethylformamide in a carbonate buffer (1 M) at pH 9; the mixture is incubated at 20° C. for 30 minutes.

The reaction mixture is purified on an exclusion column (NAP PHARMACIA) and the pyr-$T_{10}$-bio conjugate (Rt=23 minutes) is separated from the residual pyr-$T_{10}$-NH2 oligonucleotide (Rt=18 minutes) by means of analytical HPLC runs carried out under the conditions of Example 3. The fractions are detected at 265 nm.

EXAMPLE 6
Electropolymerization of the Pyr-$T_{10}$-Peptide and Pyr-$T_{10}$-Biotin Conjugates The conjugates, which have been synthesized as described in Examples 4A), 4B) and 5, are deposited, by means of electropolymerization, on gold-covered silicon microelectrodes.

These microelectrodes are arranged so as to create a matrix in "draught-board" form; this matrix is formed from square microelectrodes with 50 μm sides arranged in 5 columns and 4 rows in accordance with the following scheme (n=5 columns and p=4 rows). The microelectrodes are identified by their co-ordinates (i;j).

The electropolymerization is carried out by immersing the electrode matrix in a medium containing the pyrrole-oligonucleotide conjugate biomolecule concerned, and pyrrole (molar ratio of pyrrole/conjugate=approximately 10,000) in an 0.1 M solution of $LiClO_4$. The electrode onto which it is desired to effect the deposition is connected to a potentiostat, and cycles of between −0.35 V and +0.85 V (potentials measured in relation to a calomel electrode connected to the electrolytic cell and connected to the potentiostat) are carried out at a rate of 100 mV/s. The counterelectrode consists of a platinum wire.

Some of the microelectrodes are covered with a copolymer formed from polypyrrole and a conjugate:

pyr-$T_{10}$-ACTH (18-39): electrodes (1;4) and (3;4)

pyr-$T_{10}$-bio: electrodes (2;3) and (4;4).

The remaining electrodes are either left in their initial state, ie. the gold deposit remains unchanged (GOLD), or else covered with unmodified polypyrrole (PP); these electrodes constitute negative controls which make it possible to assess the specificity of the reactions carried out on the matrix.

Table I below shows the microelectrode matrix, and the location of the different deposits, in diagram form.

TABLE I

| | | | j | | |
|---|---|---|---|---|---|
| i | 1 | 2 | 3 | 4 | 5 |
| 1 | GOLD | GOLD | GOLD | ACTH | GOLD |
| 2 | GOLD | GOLD | BIO | GOLD | GOLD |
| 3 | PP | PP | PP | ACTH | PP |
| 4 | PP | PP | PP | BIO | PP |

GOLD: no deposit
PP: polypyrrole deposit

EXAMPLE 7
Demonstration of Electropolymerized Biomolecules on the Electrodes The electrode matrix constructed in Example 6 is incubated in the presence of a streptavidin-phycoerythrin conjugate (1 mg/ml MOLECULAR PROBES commercial solution of streptavidin-R-phycoerythrin diluted 1/20 in 10 mM phosphate buffer, pH 7.4, containing 0.5M NaCl and 0.05% TWEEN 20).

Observation under an epifluorescence microscope reveals that the fluorescence is located on electrodes (2;3) and (4;4). There is no interfering fluorescence on the other electrodes, demonstrating that the pyrrole-oligonucleotide-biotin conjugate attached specifically to the desired target electrodes.

The same microelectrode matrix is incubated in the presence of a biotinylated antibody which is specific for the C-terminal moiety of the ACTH 18-39 peptide (ACR-17-bio antibody: CIS BIO INTERNATIONAL) and then in the presence of a streptavidin/phycoerythrin conjugate in order to reveal the product of the reaction.

Observation under an epifluorescence microscope reveals that only the microelectrodes carrying the pyrrole-oligonucleotide-ACTH conjugate and those carrying biotin are fluorescent, demonstrating that the pyrrole-oligonucleotide-ACTH conjugate attached specifically to the desired target electrodes, that it is accessible to an antibody and that its antigenic properties have been retained.

EXAMPLE 8

Using the method described in Example 4, the ACTH(18-39) fragment is coupled to an oligonucleotide-pyrrole ester of N-hydroxysuccinimide which has been prepared, using the method described in Example 3, from an oligonucleotide-pyrrole which has the sequence 5'pyr-$T_9$-NH2 and which was synthesized in accordance with the protocol described in Example 2.

The following conjugates of the P-O-M type are thus available:

| I. | pyr-$T_{10}$-ACTH(11–24) |
|---|---|
| II. | pyr-$T_{10}$-ACTH(18–39) |
| III. | pyr-$T_9$-ACTH(18–39) |
| IV. | pyr-$T_{10}$-biotin |
| V. | pyr-$T_5$-HCVG(formed by combining a $T_5$ arm and a specific sequence of the genome of the HCV virus). |

Following the electropolymerization method described in Example 6, conjugates I to V are electrochemically deposited on a lattice of square microlectrodes having sides of 100 μm.

Table II below depicts the microelectrode lattice, and the location of the different deposits, in diagram form.

Some electrodes are left uncovered (GOLD) or covered with unmodified polypyrrole (PP).

TABLE II

| | | | | | j | | | |
|---|---|---|---|---|---|---|---|---|
| i | 1 | 2 | 3 | 4 | 5 | 6 | 7 | 8 |
| 1 | GOLD | IV | I | I | III | GOLD | V | PP |
| 2 | PP | III | II | II | IV | GOLD | V | GOLD |

This microelectrode plate is incubated with an oligonucleotide probe which has the sequence $dC^{biotin}(dA)_9$ and which was prepared and purified in accordance with Example 2 using the phosphoramidite biotin described by ROGET et al. [Nucleic Acids Res., 17, 7643–7650 (1989)].

The hybridization is carried out, at 20° C. for 30 min and then at 4° C. for 30 min, using approximately 8 pmol of oligonucleotide probe in 200 μl of hybridization buffer (0.1M phosphate buffer, pH 7.4, containing 0.5 M NaCl/TWEEN.

Visualization is then effected by incubating (at 4° C. for 10 min) in a solution of streptavidin-phycoerythrin (1 mg/ml MOLECULAR PROBES commercial solution of streptavidin-R-phycoerythrin) which has been diluted 1/20 in hybridization buffer.

After examination under a fluorescence microscope, it is observed that, while electrodes (1;2) and (2;5) are strongly positive and electrodes (1;3), (1;4), (2;3) and (2;4) are positive, electrodes (1;5) and (2;2) exhibit a weaker fluorescence; all the other electrodes, including (1;7) and (2;7), do not exhibit any fluorescence above the background noise.

Conjugate IV (pyr-$T_{10}$-biotin) serves as a positive visualization control. It guarantees visualization by the streptavidin/phycoerythrin complex when the plate is used for the first time. The 4 microelectrodes carrying the P-O-M-type conjugate in which O is an oligonucleotide having the $T_{10}$ sequence, i.e. (1;3), (1;4), (2;3) and (2;4), exhibit a positive hybridization, thereby guaranteeing that the P-O-M-type compound was copolymerized on these electrodes.

The weak hybridization observed on electrodes (1;5) and (2;2), and the absence of hybridization on electrodes (1;7) and (2;7), demonstrate the selectivity of the hybridization and illustrate the lower limit for the size of the oligonucleotide moiety of the conjugate which permits this dilution [sic] by hybridization to be effected and which may be estimated to be a length of between 5 and 9 nucleotides.

EXAMPLE 9

The P-O-M-type conjugate Pyr-$T_{10}$-Bio described in Example 5 is used in solution in water at a concentration of 140 $A_{265}$U/ml, enabling the molar concentration, that is 1.17 μmol/ml (where $\epsilon_{265}$=120,000) to be determined due to the UV-absorbing properties of the O moiety of this conjugate.

A range of consecutive dilutions of the conjugate (1/5; 1/25; 1/50; 1/250; 1/1250) is prepared in water, and 10 μl of each dilution is added to 300 μl of a 20 mM solution of pyrrole in 0.1M LiClO$_4$.

Copolymerizations are carried out on microelectrodes, as described in Example 6, using solutions containing varying concentrations of the pyr-$T_{10}$-Bio conjugate. The pyrrole/conjugate molar ratio is different for each electrode.

Table III below shows the microelectrode lattice and the location of different deposits, in diagram form.

TABLE III

| | | | j | | | |
|---|---|---|---|---|---|---|
| i | 1 | 2 | 3 | 4 | 5 | 6 |
| 1 | GOLD | 1/5 | 1/25 | 1/50 | 1/250 | 1/1250 |
| 2 | PP | 1/5 | 1/25 | 1/50 | 1/250 | 1/1250 |

Visualization is effected by incubating a 1/20 solution of streptavidin/phycoerythrin in a 10 mM phosphate buffer, pH 7.4, containing 0.5M NaCl and 0.05% Tween 20.

The electrode plate is observed under an epifluorescence microscope which is coupled to a CCD (HAMAMATSU) camera which is itself connected to a microcomputer equipped with an image analysis program.

The time of exposure can be arranged in order to vary the sensitivity of the detection.

Using exposure times of 0.5 s, 1 s, 2 s, 4 s, 8 s and 16 s, it is observed that at least the three contiguous contacts (1;2), (1;3) and (1;4) always give fluorescent signals which are of increasing intensity (1;2>(1;3)>1;4). Contacts (1;1) and (2;1 [sic]) give the background noise value).

The signals supplied by each member of the contact pairs (1;2) and (2;2), (1;3) and (2;3), etc. are of the same order, giving an indication of the reproducibility.

This demonstrates that the fluorescence intensities are correlated with the initial quantities of P-O-M-type compound (originally quantified by absorption at 265 nm) introduced into the different electrolyte solutions.

EXAMPLE 10 a) Variable quantities of a pyrrole-oligonucleotide conjugate (pyrrole-$T_{10}$-k-ras), having the formula Pyr-5'($T_{10}$)-k-ras$_{(28-41)}$, in which (28-41) represents the sequence of nucleotides 28 to 41 of the sense strand of the human k-ras sequence carrying a G→A mutation at nucleotide 34, were electropolymerized, as described in Example 6, in the presence of a constant quantity of pyrrole (600 μl of 20 mM pyrrole in LiClO$_4$, that is 1.2×10$^{-5}$ mol), onto 5 different microelectrodes of a plate of gold-covered square microelectrodes (50 μm×50 μm), as indicated in Table IV below.

TABLE IV

| Deposit | Quantity of conjugate | Pyrrole/conjugate ratio |
|---|---|---|
| 1 | 3 × 10$^{-9}$ mol | 4 000 |
| 2 | 6 × 10$^{-10}$ mol | 20 000 |
| 3 | 1.2 × 10$^{-10}$ mol | 10$^5$ |
| 4 | 2.4 × 10$^{-11}$ mol | 5 × 10$^5$ |
| 5 | 4.3 × 10$^{-12}$ mol | 2.5 × 10$^6$ | b) The same procedure is carried out on 5 other microelectrodes of the same plate using the P-O-M-type conjugate pyrrole-$T_{10}$-biotin and employing the range shown in Table V below and in FIG. 1:

TABLE V

| Deposit | Quantity of conjugate | Pyrrole/conjugate ratio |
|---|---|---|
| 1 | 6.6 × 10$^{-9}$ mol | 1800 |
| 2 | 6.6 × 10$^{-10}$ mol | 18000 |
| 3 | 1.3 × 10$^{-10}$ mol | 9 × 10$^4$ |

TABLE V-continued

| Deposit | Quantity of conjugate | Pyrrole/conjugate ratio |
|---|---|---|
| 4 | $2.6 \times 10^{-11}$ mol | $4.5 \times 10^5$ |
| 5 | $5.3 \times 10^{-12}$ mol | $2.25 \times 10^6$ |

The plate is incubated, at 45° C. for 30 min, in the presence of the 5'-biotinylated oligonucleotide which is complementary to the k-ras$_{(28-41)}$ sequence. A $2A_{260}$U/ml solution of biotinylated oligonucleotide is used, with this solution being diluted 1/1000 in 10 mM PBS buffer, pH 7.4, containing 0.5M NaCl and 10 mM EDTA. After washing (20° C.) with 10 mM PBS buffer containing 0.5M NaCl and 0.05% TWEEN 20, the plate is incubated (at 20° C. for 10 min) in a solution of streptavidin-phycoerythrin (1 mg/ml MOLECULAR PROBES commercial solution of streptavidin-R-phycoerythrin) diluted 1/20 in 10 mM PBS buffer, pH 7.4, containing 0.5M NaCl and 0.05% TWEEN 20.

The plate is observed under an epifluorescence microscope (OLYMPUS) which is equipped with a CCD camera (integration time $t_i$=2s; gain=×4) linked to a computer which is equipped with image analysis software (IMAGE PRO).

The fluorescence measurements obtained with the ranges of the pyrrole-$T_{10}$-k-ras and pyrrole-$T_{10}$-biotin conjugates are shown in FIG. 1: (———=k-ras; —•—=biotin), which depicts the fluorescence on each electrode plotted against the initial quantity of conjugate present in the cell during the electropolymerization and therefore the pyrrole/conjugate molar ratio.

This experiment demonstrates that choosing the pyrrole/P-O-M or pyrrole/oligonucleotide molar ratio makes it possible to control the quantity of molecules grafted to each electrode.

EXAMPLE 11

A Pyr-$T_{10}$-biotin conjugate is deposited, by electropolymerization and in accordance with the protocol described in Example 6, on a microelectrode matrix formed from 50 μm square electrodes (see Example 6), and following the arrangement (represented by the i/j coordinates) indicated on the first 2 lines of Table VI below. 2 series of identical depositions, $B_n$ and $B_n'$, are effected; depositions $B_1$ and $B_1'$ are carried out consecutively using two solutions prepared from the same solution of conjugate; the electrode and the cell are rinsed between each deposition. The same procedure is adopted with $B_2$ and $B_2'$, etc. Each series of depositions is carried out using 5-fold dilutions (in water), such as $[B_2]=[B_1]/5$; $[B_3]=[B_2]/5$. These dilutions are obtained from a parent solution of Pyr-$T_{10}$-biotin whose concentration is estimated to be 125 mmol/l ($OD_{265}$ measurement, taking $\epsilon_{265}$=120,000). 8 μl of each dilution is used in 600 μl of electropolymerization solution (20 mM pyrrole in 0.1M LiClO$_4$). The concentrations of Pyr-$T_{10}$-biotin conjugate (C), the [Pyrrole]/[Pyr-$T_{10}$-biotin] ratios (R), and the quantities of Pyr-$T_{10}$-biotin conjugate which are initially present in the electropolymerization cell, are shown in Table VI below for each $B_1/B_1'$; $B_2/B_2'$; etc. group.

TABLE VI

| | | | | j | | | |
|---|---|---|---|---|---|---|---|
| i | 1 | 2 | 3 | 4 | 5 | 6 | 7 |
| 1 | GOLD | $B_1$ | $B_2$ | $B_3$ | $B_4$ | $B_5$ | GOLD |
| 2 | GOLD | $B_1'$ | $B_2'$ | $B_3'$ | $B_4'$ | $B_5'$ | GOLD |
| C(μmol/l) | — | 125 | 25 | 5 | 1 | 0.2 | — |
| R | — | $1.2 \times 10^4$ | $6 \times 10^4$ | $3 \times 10^5$ | $1.5 \times 10^6$ | $7.5 \times 10^6$ | — |
| Q(mol) | — | $1 \times 10^{-9}$ | $2 \times 10^{-10}$ | $4 \times 10^{-11}$ | $8 \times 10^{-12}$ | $1.6 \times 10^{-12}$ | — |

After washing the electrode plate, visualization is effected by incubating in the presence of a streptavidin-phycoerythrin conjugate (at 20° C. for 10 min, commercial solution diluted 1/10 in 10 mM PBS buffer, pH 7.4, containing 0.5M NaCl and 0.05% TWEEN 20).

After rinsing with the same buffer, the plate is observed under a fluorescence microscope which is equipped with a CCD HAMAMATSU camera and IMAGE PRO image analysis software (integration time $t_i$=2 s; gain×4). Using this software, it is possible to measure the fluorescence of each deposit point by point.

Figure 2:
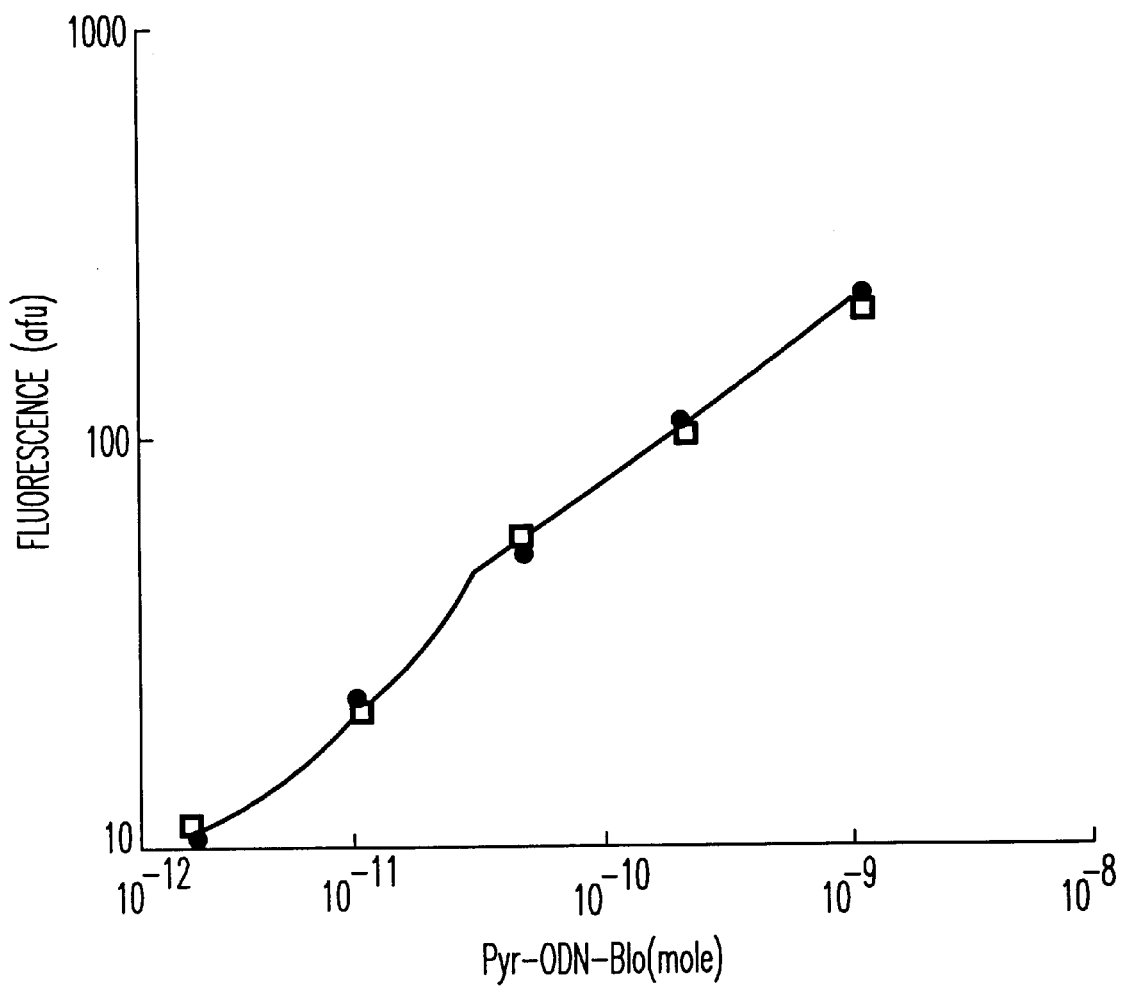

The results are shown in Table VII below, where the fluorescence is shown for each deposit in arbitrary fluorescence units (AFU) in accordance with the coordinate system (i;j) of Table VI, and in FIG. 2, which depicts the fluorescence in AFU plotted against the initial quantity of Pyr-$T_{10}$-biotin conjugate in the electropolymerization cell (=B series; •—=B' series).

TABLE VII

| | | | | j | | | |
|---|---|---|---|---|---|---|---|
| i | 1 | 2 | 3 | 4 | 5 | 6 | 7 |
| 1 | 10 | 206 | 97 | 55 | 21 | 21 | 11 |
| 2 | 11 | 208 | 100 | 51 | 22 | 12 | 9 |

These results clearly demonstrate a relationship of direct proportionality between the response (fluorescence) and the initial quantity of pyrrole-$T_{10}$-biotin conjugate (or the initial [pyrrole]/[pyr-$T_{10}$-biotin] ratio since the concentration of pyrrole is constant) in the electropolymerization mixture.

The use of compound [sic] of the P-O-M type therefore makes it possible to monitor the quantity of pyrrole (pyr-$T_{10}$-bio) conjugate which is present in an electrolyte solution in a simple manner and to prepare calibration ranges for electrode matrices.

What is claimed is:

1. A macromolecule of the formula (I):

P-O-M    (I)

in which:
- M represents a molecule of interest selected from the group consisting of a protein, a peptide, an amino acid, a glycopeptide, a lipid, a steroid, a glycolipid, a sugar and a polysaccharide;
- O represents an oligonucleotide chain;
- P represents a monomer of an electronically conductive polymer.

2. The macromolecule according to claim 1, wherein the monomer P represents a pyrrole group.

3. The macromolecule according to claim 1, wherein the oligonucleotide chain O consists of a single-stranded oligonucleotide.

4. The macromolecule according to claim 1, wherein the oligonucleotide chain O consists of an oligonucleotide which is double-stranded along at least a part of its length.

5. The macromolecule according to claim 1, wherein the oligonucleotide chain O comprises at least 6 nucleotides and in that its percentage of (G+C) is less than or equal to 70%.

6. A process for preparing a macromolecule P-O-M of the formula (I):

P-O-M    (I)

in which:
- M represents a molecule of interest;
- O represents an oligonucleotide chain;
- P represents a monomer of an electronically conductive polymer,
- from a mixture which comprises the said macromolecule and also the P-O and M reagents from which it was formed, which process comprises at least one step during which the said mixture is fractionated by any means which make it possible to separate the fractions comprising M and P-O-M, respectively, from the fraction comprising P-O, and a step during which the fraction comprising P-O-M is detected and/or the quantity of P-O-M is determined by detecting and/or measuring a parameter which is associated with the oligonucleotide O and not associated with the molecule of interest M.

7. The process according to claim 6, wherein the said parameter which is associated with the oligonucleotide O and not associated with the molecule of interest M is absorption in the ultraviolet at a wavelength of between 240 and 270 nm.

8. A copolymer, wherein at least one of its units consists of a macromolecule according to claim 1.

9. An electrode, wherein its surface carries at least one copolymer according to claim 8.

10. An electrode matrix, which comprises at least one electrode whose surface carries at least one copolymer, wherein at least one of the units of said copolymer consists of a macromolecule according to claim 1.

11. The electrode matrix according to claim 10, which comprises at least two electrodes which differ from each other in at least one of the monomers P, the oligonucleotides O and/or the molecules M which are present on their surface.

12. The electrode matrix according to claim 10, which comprises at least two electrodes which differ from each other in the quantity of oligonucleotides O and/or molecules M per unit of surface area.

13. The electrode matrix according to claim 10, which additionally comprises at least one electrode which is covered with an ECP/oligonucleotide copolymer.

14. A method of monitoring the attachment of at least one molecule X to an electrode, comprising:

electropolymerizing a copolymer on a surface of an electrode wherein at least one of the monomer units of said copolymer consists of a macromolecule of the formula (I):

P-O-M    (I)

in which:
- M represents a molecule of interest;
- O represents an oligonucleotide chain;
- P represents a monomer of an electronically conductive polymer,
- contacting said electrode having said copolymer on the surface with said molecule X,
- wherein said molecule X comprises at least one of the constituents P, O or M of a macromolecule of formula (I) and said monitoring is qualitative and/or quantitative.

15. The method of claim 14, wherein said copolymer and said molecule X are on the same electrode.

16. The method of claim 14, wherein said copolymer and said molecule X are on two different electrodes.

17. The method of claim 16, wherein the two different electrodes belong to two different matrices.

* * * * *